United States Patent [19]

Mukaiyama et al.

[11] 4,383,122
[45] May 10, 1983

[54] PROCESS FOR PREPARING α-HYDROXYALDEHYDE

[75] Inventors: Teruaki Mukaiyama, Tokyo; Yoji Sakito, Musashino; Masatoshi Asami, Yokohama, all of Japan

[73] Assignee: Sumitomo Chemical Company, Limited, Osaka, Japan

[21] Appl. No.: 257,587

[22] Filed: Apr. 27, 1981

Related U.S. Application Data

[62] Division of Ser. No. 89,356, Oct. 30, 1979, Pat. No. 4,337,346.

[30] Foreign Application Priority Data

| Nov. 2, 1978 [JP] | Japan | 53-135511 |
| Nov. 6, 1978 [JP] | Japan | 53-137147 |
| Jun. 4, 1979 [JP] | Japan | 54-70365 |
| Jun. 4, 1979 [JP] | Japan | 54-70366 |
| Jun. 4, 1979 [JP] | Japan | 54-70367 |

[51] Int. Cl.$^3$ .......................................... C07C 45/56
[52] U.S. Cl. .................................. 568/436; 568/483; 556/436
[58] Field of Search ............................. 568/436, 483; 260/326.5 CA; 556/436

[56] References Cited

U.S. PATENT DOCUMENTS

4,131,623 12/1978 Meyers ............................... 568/436

OTHER PUBLICATIONS

Chemistry Letters, No. 6, 1979, T. Mukaiyama et al., "Versatile Method for the Preparation of Optically Active Alpha-Hydroxy Aldehydes with Desired Configurations", pp. 705–708.
Chemistry Letters, No. 8, 1979, Y. Sakito et al., "Asymmetric Synthesis of Two Enantiomers of Frontalin", pp. 1027–1028.
Wanzlick et al., Chem. Ber., vol. 86, (1953), 1463–1466.
Eliel et al., Jour. Amer. Chem. Soc., vol. 100, No. 5, Mar. 1978, 1614–1616.
Mukaiyama et al., Chemistry Letters, Nov. 1978, 1253–1256.
Beilsteins Handbuch der Organischen Chemie, 4th Ed., 3rd Sup., vol. 8, part 2, (1969), Formula III, p. 1367.
Blumbergs et al., Jour. Org. Chem., vol. 37, No. 8, (1972), 1248–1251.
Synthesis, 454–455, (1976).
Tetrahedron Letters, No. 26, 2681–2684, (1972).
Helv. Chim. Acta, 61, 1903–1911, (1978).
"Compendium of Organic Synthetic Methods", vol. 2, pp. 284–287, (1974).
Tetrahedron Letters, 22, 2855–2858, (1981).
J. Org. Chem., 44, 3598–3599, (1979).

*Primary Examiner*—Bernard Helfin
*Attorney, Agent, or Firm*—Stevens, Davis, Miller & Mosher

[57] ABSTRACT

An optically active or racemic α-hydroxyaldehyde represented by the general formula (2),

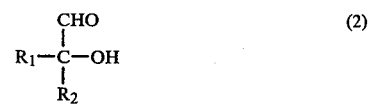
(2)

wherein $R_1$ represents a $C_6$–$C_{14}$ aryl group, $C_1$–$C_{10}$ alkyl group, $C_3$–$C_{10}$ alkenyl group, $C_2$–$C_{10}$ alkynyl group, $C_7$–$C_{14}$ aralkyl group, or a group containing a functional group in the organic portion of said groups and $R_2$ represents a $C_1$–$C_{10}$ alkyl group, $C_2$–$C_{10}$ alkenyl group, $C_2$–$C_{10}$ alkynyl group, $C_7$–$C_{14}$ aralkyl group, $C_6$–$C_{14}$ aryl group, or a group containing a functional group in the organic portion of these groups, which is an important intermediate for preparation of pharmaceuticals and agricultural chemicals, and prepared by allowing an optically active or racemic compound represented by the general formula (1),

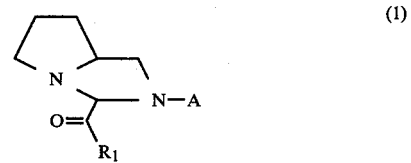
(1)

(wherein A represents a $C_6$–$C_{14}$ aryl group or a $C_1$–$C_4$ alkyl or alkoxy group- or halogen-substituted $C_6$–$C_{14}$ aryl group and $R_1$ is as defined above) to react with a Grignard reagent, and thereafter hydrolyzing the reaction product.

6 Claims, No Drawings

PROCESS FOR PREPARING α-HYDROXYALDEHYDE

This is a division of application Ser. No. 89,356 filed Oct. 30, 1979 and now U.S. Pat. No. 4,337,346.

This invention relates to a process for preparing an aldehyde, particularly an optically active or racemic α-hydroxyaldehyde by the reaction between a novel optically active or racemic compound (hereinafter referred to as an aminal) represented by the general formula (1),

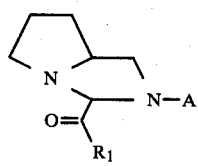

wherein A represents a $C_6$–$C_{14}$ aryl group or a $C_1$–$C_4$ alkyl or alkoxy group- or halogen-substituted $C_6$–$C_{14}$ aryl group and $R_1$ represents a $C_6$–$C_{14}$ aryl, $C_1$–$C_{10}$ alkyl (preferably $C_2$–$C_{10}$ alkyl), $C_3$–$C_{10}$ alkenyl, $C_2$–$C_{10}$ alkynyl, or $C_7$–$C_{14}$ aralkyl group or a group containing a functional group (preferably, silyloxy group, $C_1$–$C_4$ alkoxy group) in the organic portion of said groups and a Grignard reagent and subsequent hydrolysis of the reaction product.

This invention further relates to said aminal and a process for producing the same.

The α-hydroxyaldehydes prepared according to this invention can be used as intermediates for the preparation of pharmaceuticals and agricultural chemicals. Particularly, the process for preparing optically active α-hydroxyaldehydes is of great significance. For instance, atrolactamide derivable from 2-hydroxy-2-phenylpropionaldehyde is used as a pharmaceutical. These intermediates, furthermore, are used also in synthesizing frontalin and derivatives thereof which are aggregation pheromones.

There are few precedents for the preparation of optically active α-hydroxyaldehydes. In J. Amer. Chem. Soc., 100, 1514 (1978), there is described a method for preparing 2-hydroxy-2-phenylpropionaldehyde derivatives. This method, however, has disadvantages in that the preparation of an optically active starting material is not easy, a large number of preparative steps are required and the optical purity of the final product does not exceed 44%.

The present inventors, as a result of extensive studies, have succeeded in developing a process for preparing α-hydroxyaldehydes having a high optical purity, as described below, by the use of novel aminal compounds in accomplishing this invention.

An object of this invention is to provide a process for preparing an optically active or racemic α-hydroxyaldehyde and to provide a novel α-hydroxyaldehyde and a derivative thereof.

Another object of this invention is to provide an aminal and a process for preparing the same and to provide a novel aminal precursor.

Other objects and advantages of this invention will become apparent from the following description.

According to this invention, there is provided a process for preparing an α-hydroxyaldehyde represented by the general formula (2),

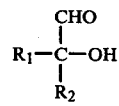

(wherein $R_1$ is as defined above and $R_2$ represents a $C_1$–$C_{10}$ alkyl group (preferably, $C_2$–$C_{10}$ alkyl group), $C_2$–$C_{10}$ alkenyl group, $C_2$–$C_{10}$ alkynyl group, $C_7$–$C_{14}$ aralkyl group, $C_6$–$C_{14}$ aryl group, or a group containing a functional group (preferably a silyloxy or $C_1$–$C_4$ alkoxy group) in the organic portion of these groups) and a derivative thereof, which comprises allowing an optically active or racemic aminal represented by the general formula (1),

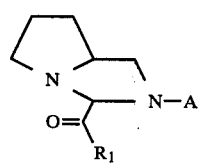

(wherein A and $R_1$ are as defined above) to react with a Grignard reagent represented by the formula, $R_2MgX$ (wherein $R_2$ is as defined above and X is a halogen atom such as Cl, Br or I) and then hydrolyzing the reacton product. Most preferably, optically active or racemic α-hydroxyaldehydes are obtained when $R_1$ and $R_2$ are different from each other.

Further, according to this invention there is provided a process for preparing the above-said aminal by allowing an arylglyoxal to react with an optically active or racemic 2-(N-substituted aminomethyl)-pyrrolidine represented by the general formula (3),

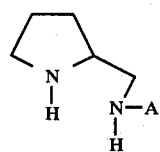

wherein A is as defined above; or by allowing a Grignard reagent represented by the formula, $R_1MgX$ (wherein $R_1$ and X are as defined above) to react with an optically active or racemic diazabicyclooctane derivative represented by the general formula (4),

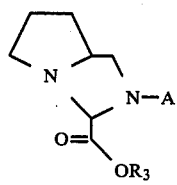

wherein A is as defined above and $R_3$ represents a $C_1$–$C_4$ alkyl group.

Still further, according to this invention, the diazabicyclooctane derivative represented by the formula (4) is a novel compound and can be obtained by allowing a glyoxylate ester or a glyoxylate ester hemiacetal to react with the above-said optically active or racemic 2-(N-substituted aminomethyl)pyrrolidine represented by the general formula (3).

The invention is described below in detail.

First, glyoxylate esters or glyoxylate ester hemiacetals used in preparing diazabicyclooctane derivatives represented by the formula (4) are generally $C_1-C_4$ alkyl esters such as, for example, methyl glyoxylate, ethyl glyoxylate, n-propyl glyoxylate, isopropyl glyoxylate, n-butyl glyoxylate, methyl hydroxymethoxyacetate, ethyl hydroxyethoxyacetate, n-propyl hydroxy-n-propoxyacetate, isopropyl hydroxyisopropoxyacetate, n-butyl hydroxy-n-butoxyacetate and the like. The alkyl groups of these esters correspond to $R_3$ in the general formula (4).

2-(N-substituted aminomethyl)pyrrolidines can be prepared easily, for example, from proline [Bull. Chem. Soc., Japan, 51, 1869 (1978)]. The most preferably used are those of the general formula (3) in which A is a $C_6-C_{14}$ aryl group or a $C_1-C_4$ alkoxy or halogen-substituted $C_6-C_{14}$ aryl group, such as, for example, 2-(anilinomethyl)pyrrolidine, 2-(2,6-xylidinomethyl)-pyrrolidine, 2-(N-p-tolylaminomethyl)pyrrolidine and 2-(N-naphthylaminomethyl)pyrrolidine.

Diazabicyclooctane derivatives represented by the general formula (4) are prepared by the reaction between optically active or racemic 2-(N-substituted aminomethyl)pyrrolidines and glyoxylate esters or glyoxylate ester hemiacetals. This reaction is carried out generally in the presence of a common organic solvent such as benzene, toluene, ether, chloroform, hexane, heptane or the like. Although the reaction temperature is subject to no particular limitation, it is generally in the range of $-30°$ to $200°$ C. and preferably below the boiling point of the solvent employed. If the reaction is carried out at a temperature higher than the boiling point of the solvent, the reaction system must be kept under a superatmospheric pressure in a closed vessel. The water formed with the progress of reaction should be removed by the use of a dehydrating agent such as a molecular sieve or by azeotropic distillation. The removal of water by azeotropic distillation with benzene or toluene is convenient and economical. The diazabicyclooctane derivative of the formula (4) thus obtained can be purified by column chromatography or distillation, but a crude product obtained after removal of the solvent by distillation can be used without further purification. Examples of diazabicyclooctane derivatives obtainable in the above manner include, besides 2-methoxycarbonyl-3-phenyl-1,3-diazabicyclo[3,3,0]octane as shown in Example below-mentioned, 2-alkoxycarbonyl-3-phenyl-1,3-diazabicyclo[3,3,0]octanes such as 2-ethoxycarbonyl-3-phenyl-1,3-diazabicyclo[3,3,-0]octane and 2-butoxycarbonyl-3-phenyl-1,3-diazabicyclo[3,3,0]octane and the like. It will be easily understood that other diazabicyclooctane derivatives can also be obtained in a similar manner.

The aminal represented by the general formula (1) used in preparing an α-hydroxyaldehyde or a derivative thereof can be obtained by the reaction of a Grignard reagent with the above-mentioned diazabicyclooctane derivative.

The Grignard reagents, as herein referred to, include common Grignard reagents such as, for example, $C_1-C_{10}$-alkylmagnesium halides, $C_{3-10}$-alkenylmagnesium halides, $C_{2-10}$-alkynylmagnesium halides, $C_{7-14}$-aralkylmagnesium halides, $C_{6-14}$-arylmagnesium halides and the like and those containing a $C_{1-4}$-alkoxy group or a silyloxy group in the organic portion of said compounds. The organic group bonded to the magnesium atom of a Grignard reagent after reaction corresponds to $R_1$ of an aminal. As the Grignard reagents used in this invention, those containing the below-described $R_1$ as the organic group are illustrated.

The yield of an aminal derivative can be improved by conducting the reaction of a Grignard reagent with an optically active or racemic diazabicyclooctane derivative of the formula (4) in the presence of a magnesium halide. The magnesium halides include magnesium iodide, magnesium bromide and magnesium chloride. Of these halides, magnesium chloride is preferred. The solvents used in the above-said reaction with a Grignard reagent are ethereal solvents used in common Grignard reactions, such as diethyl ether, tetrahydrofuran or a mixture thereof. When the Grignard reagent is reacted in the presence of a magnesium halide, it is preferable to use tetrahydrofuran as solvent. Although the reaction temperature is under no particular limitation, it is generally in the range of $-100°$ to $70°$ C. and below the boiling point of the solvent employed. Lower temperatures are preferable to reduce the by-products. In the reaction, the molar ratio of a diazabicyclooctane derivative to a Grignard reagent is generally 1:1 to 1:3, preferably 1:1 to 1:1.5.

The aminals of the formula (1) from alkylglyoxals, alkenylglyoxals, alkynylglyoxals and aralkylglyoxals are novel compounds. Examples for A of the formula (1) are aryl groups such as phenyl group, 2,6-xylyl group, p-tolyl group and naphthyl group. Further, there may be mentioned these groups substituted with a halogen or $C_1-C_4$ alkoxy group. Examples for $R_1$ include alkyl groups such as methyl group, ethyl group, n-propyl group, isopropyl group, n-butyl group, isobutyl group, n-amyl group and cyclohexyl group; alkenyl groups such as 2-propenyl group, 2-butenyl group, 3-butenyl group, 2-pentenyl group, 3-pentenyl group, 4-pentenyl group, 4-methyl-4-pentenyl group and cyclohexenyl group; alkynyl groups such as ethynyl group, propargyl group, 2-butynyl group, 2-pentynyl group and 3-pentynyl group; aralkyl groups such as benzyl group, phenethyl group and phenylpropyl group; and aryl groups such as phenyl group, p-tolyl group, 2,4-xylyl group and naphthyl group. Further, there may be mentioned these groups substituted with a silyloxy or $C_1-C_4$ alkoxy group.

The aminals of the general formula (1) in which $R_1$ is an aryl group can also be prepared in the following way:

An optically active or racemic aminal represented by the general formula (1) can be prepared by the reaction of an arylglyoxal and the aforementioned optically active or racemic 2-(N-substituted aminomethyl)pyrrolidine represented by the general formula (3). The arylglyoxals for use in the above reaction include phenylglyoxal, p-tolylglyoxal, 2,4-xylylglyoxal and naphthylglyoxal, of which phenylglyoxal is preferable. The solvents used in the above reaction are common organic solvents such as benzene, toluene, ether, chloroform, hexane, heptane and the like. The reaction temperature is subject to no particular limitation, but is generally in the range of $-30°$ to $200°$ C. and below the boiling point of the solvent employed. The reaction becomes complete more rapidly with the increase in reaction temperature. However, at a temperature exceeding the boiling point of the solvent, the reaction must be carried out under a superatmospheric pressure and is of no commercial benefit. The water formed with the progress of reaction is removed by a dehydrating agent such as a molecular sieve or by azeotropic distillation.

The dehydration by azeotropic distillation with benzene or toluene is easy and economical.

The arylglyoxal aminal can be further purified by the common technique such as recrystallization or chromatography. However, a crude product obtained after removal of the solvent by distillation is pure enough to be used directly as the starting material in preparing an α-hydroxyaldehyde or a derivative thereof described below.

An α-hydroxyaldehyde represented by the general formula (2) or a derivative thereof can be prepared by the reaction between an aminal and a Grignard reagent and succeeding hydrolysis of the reaction product.

Examples of the compounds represented by the general formula (2) are those in which $R_1$ is a group described above and $R_2$ is a $C_1$–$C_{10}$ alkyl group such as methyl group, ethyl group, n-propyl group, isopropyl group, n-butyl group, isobutyl group, n-amyl group or cyclohexyl group; a $C_2$–$C_{10}$ alkenyl group such as vinyl group, 2-propenyl group, 2-butenyl group, 3-butenyl group, 2-pentenyl group, 4-pentenyl group, 4-methyl-4-pentenyl group or cyclohexenyl group; a $C_2$–$C_{10}$ alkynyl group such as ethynyl group, propargyl group, 2-butynyl group, 2-pentynyl group or 3-pentynyl group; a $C_7$–$C_{14}$ aralkyl group such as benzyl group, phenethyl group or phenylpropyl group; or a $C_6$–$C_{14}$ aryl group such as phenyl group or p-tolyl group. Further, there may be mentioned these groups substituted with a silyloxy or $C_1$–$C_4$ alkoxy group.

The Grignard reagents for use in the above reaction can be the same as those used in preparing aminals from diazabicyclooctane derivatives represented by the formula (4). In this case, $R_2$ in the formula (4) corresponds to the organic group bonded to the magnesium atom of the Grignard reagent. Therefore, by selecting a suitable Grignard reagent, it is possible to obtain an aldehyde having an intended $R_2$. The solvent for use in the reaction involving a Grignard reagent can be an ether-type solvent commonly used in general Grignard reactions, such as diethyl ether, tetrahydrofuran or a mixture thereof. The reaction temperature is subject to no particular limitation, but is generally in the range of $-100°$ to 70° C. and below the boiling point of the solvent employed. Lower reaction temperatures are preferred to obtain a product of high optical purity. The molar ratio of an aminal to the Grignard reagent is not particularly limited, but is preferably in the range of 1:1–1:5.

The optically active α-hydroxyaldehyde is obtained by hydrolyzing the reaction product of the above Grignard reaction. It is also possible to prepare an α-hydroxyaldehyde derivative by allowing the reaction product of the Grignard reaction to react with an organic halide or the like to form a derivative having an ether group, e.g. benzyloxy group, in place of a hydroxyl group and then hydrolyzing. The hydrolysis is effected with an acid such as hydrochloric acid or sulfuric acid at a temperature in the range of generally from 0° to 100° C. In view of the stability of the α-hydroxyaldehyde to be prepared, a lower temperature is preferred.

The optically active α-hydroxyaldehyde thus obtained from (S)-2-(N-substituted aminomethyl)pyrrolidine used as an asymmetric source has R-configuration when the substituent group $R_2$ has higher priority than the substituent group $R_1$ in the general formula (2) and, conversely, S-configuration when the substituent group $R_2$ has lower priority than the substituent group $R_1$. Therefore, it is possible to prepare an α-hydroxyaldehyde having either configuration by suitably combining the substituent group $R_1$ of an aminal with the substituent group $R_2$ of a Grignard reagent used in this invention. For instance, in preparing 2-hydroxy-2-methylbutyraldehyde, R-configuration is formed when an aminal having a methyl group as $R_1$ of the general formula (1) is allowed to react with an ethyl magnesium halide, while S-configuration is formed by the reaction of an aminal having an ethyl group as $R_1$ with a methyl magnesium halide.

In general, when it is intended to prepare a compound having a reverse configuration to that of the product obtained by asymmetric synthesis, frequently an enantiomer must be used as the asymmetric source. This is a commercial disadvantage, because in most of the cases, the desired enantiomer is not available or is very expensive if available. According to this invention an α-hydroxyaldehyde having any configuration can be prepared by the suitable combination of an aminal with a Grignard reagent and, moreover, 2-(N-substituted aminomethyl)pyrrolidine can be recovered by extracting with an organic solvent the neutralized aqueous layer resulting from the hydrolysis. The recovered material shows NMR spectrum and IR spectrum identical with those of the starting material. This is one of the advantages of this invention, because an aminal can be repeatedly prepared by using the recovered 2-(N-substituted aminomethyl)pyrrolidine.

The invention is illustrated below in detail with reference to Examples.

EXAMPLE 1

In 10 ml of benzene, were dissolved 505 mg of (S)-2-(anilinomethyl)pyrrolidine and 436 mg of phenylglyoxal monohydrate. The resulting solution was refluxed for one hour while removing the formed water by azeotropic distillation. After removal of benzene by distillation in vacuo, the residue was allowed to crystallize at $-20°$ C. After recrystallization from 2 ml of methanol, 700 mg (84%) of an aminal of phenylglyoxal were isolated.

| Elementary analysis: | C % | H % | N % |
|---|---|---|---|
| Found | 78.26 | 6.96 | 9.36 |
| Calculated ($C_{19}H_{20}N_2O$) | 78.05 | 6.90 | 9.58 |

Melting point: 101°–102° C.

EXAMPLE 2

In 15 ml of benzene, were dissolved 714 mg of phenylglyoxal monohydrate and 828 mg of (S)-2-(anilinomethyl)pyrrolidine. The resulting solution was refluxed for one hour while removing the formed water by azeotropic distillation. Benzene was removed by distillation in vacuo and the residue was dissolved in 20 ml of ether. To the resulting solution cooled to $-70°$ C., was added dropwise 1.5 equivalents of an ether solution of methylmagnesium iodide. After having been allowed to react for one hour at $-70°$ C., the solution was admixed with 4 ml of saturated aqueous ammonium chloride solution and brought to room temperature. After separating the ether layer, the aqueous layer was neutralized with saturated aqueous sodium hydrogencarbonate solution and then extracted with ether. The ether layer was combined with the previously separated ether layer, admixed with 30 ml of 2% hydrochloric acid and allowed to react for 12 hours at 0° C. The ether layer was separated, washed with saturated aqueous sodium chloride solution, and dried over anhydrous sodium sulfate. After removal of the ether by distillation in vacuo, the residue was purified by means of a silica gel column chromatography to obtain 471 mg (67%) of (S)-(+)-2-hydroxy-2-phenylpropionaldehyde. $[\alpha]_D = +244°$ (C=1.138, benzene); optical yield was 95%. The optical yield was determined by converting the substance into methyl atrolactate methyl ether of known optical rotation.

EXAMPLE 3

The procedure of Example 2 was repeated, except that ethylmagnesium iodide was used as the Grignard reagent. There were obtained 584 mg (76%) of (S)-(+)-2-hydroxy-2-phenylbutyraldehyde; $[\alpha]_D = +239°$ (C=1.048, benzene); optical yield, 94%. The optical yield was determined by converting the substance into 2-phenylbutane-1,2-diol of known optical rotation. The aqueous layer obtained after removal of the ether from the hydrolyzate mixture was made alkaline with an aqueous sodium hydroxide solution and extracted with ether. After removal of the solvent by distillation, the residue was distilled to recover 84% of (S)-2-(anilinomethyl)pyrrolidine.

EXAMPLE 4

The procedure of Example 2 was followed, except that isopropylmagnesium iodide was used as the Grignard reagent. There were obtained 686 mg (82%) of (S)-(+)-2-hydroxy-2-phenyl-3-methylbutyraldehyde; $[\alpha]_D = +310°$ (C=1.031, benzene); optical yield, 95% or more. NMR peaks: $\delta(ppm) = 0.7$ (3H, doublet), 0.9 (3H, doublet), 2.4 (1H, multiplet), 3.6 (1H, singlet), 7.3 (5H, multiplet), 9.4 (1H, singlet). The optical yield was determined by reducing (S)-(+)-2-hydroxy-2-phenyl-3-methylbutyraldehyde to (S)-(−)-2-phenyl-3-methylbutane-1,2-diol, condensing the hydroxyl group at position 1 of the latter with (+)-α-methoxy-α-trifluoromethylphenylacetyl chloride to form an ester, and measuring NMR spectra of the diastereomer.

EXAMPLE 5

The procedure of Example 2 was followed, except that vinylmagnesium bromide was used as the Grignard reagent and THF as the solvent. There were obtained 510 mg (67%) of (S)-(+)-2-hydroxy-2-phenyl-3-butenal, which is a novel compound; $[\alpha]_D = +179°$ (C=0.983, benzene); optical yield: 94%. NMR peaks: $\delta(ppm) = 3.9$ (1H, singlet), 5.2–5.6 (2H, multiplet), 6.0–7.4 (1H, multiplet), 7.2 (5H, singlet), 9.4 (1H, singlet). The optical yield was determined by converting to 2-phenylbutane-1,2-diol of known optical rotation.

EXAMPLE 6

Except that p-tolylmagnesium bromide was used as the Grignard reagent, the procedure of Example 2 was followed to obtain 701 mg (66%) of (−)-2-hydroxy-2-p-tolyl-2-phenylacetaldehyde, a novel compound; $[\alpha]_D = -9.0°$ (C=1.005, benzene). NMR peaks: $\delta(ppm) = 2.3$ (3H, singlet), 4.2 (1H, singlet), 7.0 (4H, singlet), 7.1 (5H, singlet).

EXAMPLE 7

Example 2 was repeated, except that 959 mg of (S)-2-(2,6-xylidinomethyl)pyrrolidine was used in place of (S)-2-(anilinomethyl)pyrrolidine and ethylmagnesium iodide was used as the Grignard reagent. There were obtained 563 mg (73%) of (S)-(+)-2-hydroxy-2-phenylbutyraldehyde; $[\alpha]_D = +214°$ (C=1.080, benzene); optical yield, 84%.

EXAMPLE 8

In 10 ml of benzene, were dissolved 683 mg of methyl hydroxymethoxyacetate and 1.00 g of (S)-2-(anilinomethyl)pyrrolidine. The resulting solution was refluxed for 30 minutes while removing the water by azeotropic distillation. On removing the solvent by distillation in vacuo, there were obtained 1.38 g of 2-carbomethoxy-3-phenyl-1,3-diazabicyclo[3,3,0]octane, a derivative of glyoxylic acid. NMR peaks: $\delta(ppm) = 1.5–2.3$ (4H, multiplet), 2.3–4.1 (5H, multiplet), 3.5 (3H, singlet), 4.6 (1H, singlet), 6.2–7.1 (5H, multiplet). After having been purified by alumina column chromatography and short-path distillation, the substance showed the following results of elementary analysis:

|  | C % | H % | N % |
|---|---|---|---|
| Found | 68.26 | 7.64 | 11.65 |
| Calculated | 68.27 | 7.37 | 11.37 |

EXAMPLE 9

Except that 500 mg of methyl glyoxylate was used in place of methyl hydroxymethoxyacetate, the procedure of Example 8 was repeated to obtain 1.38 g of 2-carbomethoxy-3-phenyl-1,3-diazabicyclo[3,3,0]octane.

EXAMPLE 10

Except that 842 mg of ethyl hydroxyethoxyacetate was used in place of methyl hydroxymethoxyacetate, the procedure of Example 8 was followed to obtain 1.44 g of 2-carboethoxy-3-phenyl-1,3-diazabicyclo[3,3,0]octane. NMR peaks: $\delta(ppm) = 1.2$ (3H, triplet), 1.5–2.3 (4H, multiplet), 2.3–4.1 (5H, multiplet), 4.0 (2H, quartet), 4.6 (1H, singlet), 6.2–7.1 (5H, multiplet).

EXAMPLE 11

Except that 740 mg of n-butyl glyoxylate was used in place of methyl hydroxymethoxyacetate, the procedure of Example 8 was followed to obtain 1.60 g of 2-carbobutoxy-3-phenyl-1,3-diazabicyclo[3,3,0]octane.
NMR peaks: $\delta(ppm) = 0.7–2.3$ (11H, multiplet), 2.3–4.1 (5H, multiplet), 3.9 (2H, triplet), 4.6 (1H, singlet), 6.2–7.1 (5H, multiplet).

EXAMPLE 12

In 7 ml of THF, was dissolved 295 mg of 2-carbomethoxy-3-phenyl-1,3-diazabicyclo[3,3,0]octane. After addition of 138 mg of anhydrous magnesium chloride, the mixture was refluxed for 10 minutes. To the mixture cooled to −70° C., was added dropwise an ether solution of 1.36 equivalents of methylmagnesium bromide. After having been stirred for 15 minutes at −70° C., the reaction mixture was admixed with saturated aqueous ammonium chloride solution and ether and brought to room temperature. The mixture was extracted with ether and the ether layer was dried. The ether layer was freed from the solvent by distillation in vacuo and the residue was purified by alumina column chromatography to obtain 199 mg (72%) of 2-acetyl-3-phenyl-1,3-diazabicyclo[3,3,0]octane. NMR peaks: $\delta(ppm) = 1.5–2.2$ (4H, multiplet), 1.9 (3H, singlet), 2.4–3.3 (3H, multiplet), 3.5–3.9 (2H, multiplet), 4.1 (1H, singlet), 6.1–7.1 (5H, multiplet).

EXAMPLE 13

2-Carbomethoxy-3-phenyl-1,3-diazabicyclo[3,3,0]octane prepared from 1.76 g of (S)-2-(anilinomethyl)pyrrolidine, as described in Example 8, was dissolved in 50 ml of THF, then admixed with 1.05 g of anhydrous magnesium chloride and refluxed by heating for 10 minutes. To the mixture cooled to $-70°$ C., was added dropwise an ether solution containing 1.46 equivalents of ethylmagnesium bromide. The resulting mixture was treated as described in Example 12 to obtain 694 mg (28%) of 2-propionyl-3-phenyl-1,3-diazabicyclo[3,3,0]octane. NMR peaks: $\delta$(ppm)=1.0 (3H, triplet), 1.4–2.1 (4H, multiplet), 2.1–2.6 (2H, multiplet), 2.6–3.3 (3H, multiplet), 3.5–3.9 (2H, multiplet), 4.2 (1H, singlet), 6.1–7.1 (5H, multiplet).

EXAMPLE 14

2-Carbomethoxy-3-phenyl-1,3-diazabicyclo[3,3,0]octane prepared from 637 mg of (S)-2-(anilinomethyl)pyrrolidine was dissolved in 18 ml of THF, then admixed with 378 mg of anhydrous magnesium chloride, and refluxed for 10 minutes by heating. To the mixture cooled to $-70°$ C., was added dropwise an ether solution containing 1.37 equivalents of isopropylmagnesium bromide. The resulting mixture was treated as in Example 12 to obtain 731 mg (79%) of 2-isobutyryl-3-phenyl-1,3-diazabicyclo[3,3,0]octane. NMR peaks: $\delta$ (ppm)=0.9 (3H, doublet), 1.1 (3H, doublet), 1.5–2.2 (4H, multiplet), 2.4–3.3 (4H, multiplet), 3.5–3.9 (2H, multiplet), 4.4 (1H, singlet), 6.2–7.1 (5H, multiplet).

EXAMPLE 15

2-Carbomethoxy-3-phenyl-1,3-diazabicyclo[3,3,0]octane prepared from 181 mg of (S)-2-(anilinomethyl)pyrrolidine was dissolved in 5.5 ml of THF, then admixed with 108 mg of anhydrous magnesium chloride, and heated and refluxed for 10 minutes. To the mixture cooled to $-70°$ C., was added dropwise 1.38 equivalents of phenylmagnesium bromide dissolved in ether. After having been stirred at $-70°$ C. for 15 minutes, the reaction mixture was admixed with saturated aqueous ammonium chloride solution and ether, and brought to room temperature. The mixture was extracted with ether and the ether layer was washed with 1 N aqueous sodium hydroxide solution and then with saturated aqueous sodium chloride solution. After drying, the ether layer was freed from the solvent by distillation under reduced pressure. The oily residue was purified by alumina column chromatography to obtain 230 mg (77%) of 2-benzoyl-3-phenyl-1,3-diazabicyclo[3,3,0]octane. NMR peaks: $\delta$ (ppm)=1.6–2.2 (4H, multiplet), 2.4–3.9 (5H, multiplet), 5.4 (1H, singlet), 6.1–7.9 (10H, multiplet).

EXAMPLE 16

In 5 ml of ether, was dissolved 99 mg of 2-carbomethoxy-3-phenyl-1,3-diazabicyclo[3,3,0]octane. To the resulting solution cooled to $-70°$ C., was added dropwise 1.2 equivalents of methylmagnesium bromide dissolved in ether. The mixture was allowed to react at $-70°$ C. for 1.5 hours, then admixed with saturated aqueous ammonium chloride solution, and the reaction mixture was brought to room temperature. The ether layer was separated, dried, and freed from the solvent by distillation under reduced pressure. The yield of 2-acetyl-3-phenyl-1,3-diazabicyclo[3,3,0]octane was 54%, as determined from the NMR spectrum.

EXAMPLE 17

In 25 ml of THF, was dissolved 720 mg of 2-carbomethoxy-3-phenyl-1,3-diazabicyclo[3,3,0]octane. After addition of 291 mg of anhydrous magnesium chloride, the mixture was refluxed for 10 minutes by heating. To the mixture cooled to $-70°$ C., was added dropwise 1.6 equivalents of 4-methyl-4-pentenylmagnesium bromide dissolved in ether. The mixture was treated as in Example 12 to obtain 378 mg (44%) of 2-(5'-methyl-5'-hexenoyl)-3-phenyl-1,3-diazabicyclo[3,3,0]octane. NMR peaks: $\delta$ (ppm)=1.6 (3H, singlet), 1.5–2.1 (8H, multiplet), 2.2–2.5 (2H, multiplet), 2.6–3.3 (3H, multiplet), 3.5–3.9 (2H, multiplet), 4.2 (1H, singlet), 4.5 (2H, broad singlet), 6.2–7.1 (5H, multiplet).

EXAMPLE 18

In 5 ml of ether, was dissolved 258 mg of 5-(S)-2-acetyl-3-phenyl-1,3-diazabicyclo[3,3,0]octane. To the resulting solution cooled to $-70°$ C., was added 2 equivalents of phenylmagnesium bromide dissolved in ether. The mixture was allowed to react for one hour, then admixed with 3 ml of saturated aqueous ammonium chloride solution, and the reaction mixture was brought to room temperature. The ether layer was separated, washed with 1 N aqueous sodium hydroxide solution, then admixed with 11 ml of 2% hydrochloric acid, and the mixture was allowed to react at 0° C. for 12 hours. The ether layer was separated, washed with saturated aqueous sodium chloride solution, and dried over anhydrous sodium sulfate. The dried mixture was freed from the ether by distillation under reduced pressure and purified by passing through a silica gel column to obtain 128 mg (76%) of (R)-2-hydroxy-2-phenylpropionaldehyde; $[\alpha]_D = -255°$ (C=1.060, benzene); optical yield, 99%.

EXAMPLE 19

In 27 ml of ether, was dissolved 1.41 g of 5-(S)-2-acetyl-3-phenyl-1,3-diazabicyclo[3,3,0]octane. To the resulting solution cooled to $-70°$ C., was added dropwise 1.5 equivalents of ethylmagnesium bromide dissolved in ether. The mixture was allowed to react at $-70°$ C. for one hour, then admixed with 10 ml of saturated aqueous ammonium chloride solution, and brought to room temperature. The ether layer was separated, washed with saturated aqueous sodium chloride solution, and dried over anhydrous sodium sulfate. The dried ether layer was freed from the ether by distillation under reduced pressure and the residue was dissolved in 20 ml of dimethylformamide.

To the solution obtained above, was added 0.53 g of sodium hydride (55%). The mixture was stirred at 60° C. for 2 hours, then admixed with 2.09 g of benzyl bromide, and allowed to react for one hour. The reaction mixture was subjected to extraction by adding water and ether. The ether layer was washed with saturated aqueous sodium chloride solution, dried over anhydrous sodium sulfate, and freed from the ether by distillation under reduced pressure. The obtained residue was purified by passing through an alumina column, then admixed with 60 ml of 2% hydrochloric acid and 60 ml of ether, and allowed to react at 0° C. for 4 hours. The ether layer was separated, washed with saturated sodium chloride solution, dried over anhydrous sodium sulfate, and freed from the ether by distillation under reduced pressure. The obtained residue was purified by the silica gel preparative TLC to obtain 506 mg (43%) of (R)-2-benzyloxy-2-methylbutyraldehyde; $[\alpha]_D = +39°$ (C=1.027, benzene); optical yield, 78%. The optical yield was determined by converting the substance to 2-methylbutane-1,2-diol of known optical rotation. NMR peaks: δ (ppm)=0.9 (3H, triplet), 1.3 (3H, singlet), 1.8 (2H, quartet), 4.4 (2H, singlet), 7.2 (5H, singlet), 9.5 (1H, singlet).

EXAMPLE 20

In 20 ml of tetrahydrofuran, was dissolved 1.00 g of 5-(S)-2-acetyl-3-phenyl-1,3-diazabicyclo[3,3,0]-octane. To the resulting solution cooled to −70° C., was added 2.7 equivalents of vinylmagnesium bromide dissolved in tetrahydrofuran. The mixture was allowed to react for 20 hours and then the reaction temperature was gradually elevated to 0° C. After addition of 10 ml of saturated aqueous ammonium chloride solution, the temperature of the reaction mixture was brought to room temperature. The reaction mixture was subjected to extraction with ether and the ether layer was washed with saturated aqueous sodium chloride solution and dried over anhydrous sodium sulfate. After removal of the solvent by distillation under reduced pressure, the residue was dissolved in 7 ml of dimethylformamide. To the resulting solution, was added 0.38 g of sodium hydride (55%). The mixture was stirred at 60° C. for 2 hours, then admixed with 1.49 g of benzyl bromide, and allowed to react for one hour. The reaction mixture was subjected to extraction by adding water and ether and the ether layer was washed with saturated aqueous sodium chloride solution, and dried over anhydrous sodium sulfate. The dried ether layer was freed from the ether by distillation under reduced pressure and the obtained residue was purified by the alumina column, admixed with 40 ml of 2% hydrochloric acid and 40 ml of ether to react at 0° C. for 12 hours. The ether layer was separated, washed with saturated aqueous sodium chloride solution and dried over anhydrous sodium sulfate. The ether was distilled off under reduced pressure and the obtained residue was purified by the silica gel preparative TLC to obtain 367 mg (44%) of (R)-2-benzyloxy-2-methyl-3-butenal; $[\alpha]_D = +156°$ (C=0.963, benzene); optical yield, 93%. The optical yield was determined by converting the substance to 2-methylbutane-1,2-diol of known optical rotation. NMR peaks: δ (ppm)=1.4 (3H, singlet), 4.4 (2H, singlet), 5.1–5.7 (3H, multiplet), 7.2 (5H, singlet), 9.3 (1H, singlet).

EXAMPLE 21

Except that 5-(S)-2-propionyl-3-phenyl-1,3-diazabicyclo[3,3,0]octane was used in place of 5-(S)-2-acetyl-3-phenyl-1,3-diazabicyclo[3,3,0]octane, Example 18 was repeated to obtain (R)-2-hydroxy-2-phenyl-butyraldehyde (80% yield); $[\alpha]_D = -256°$ (C=1.147, benzene); optical yield, 100%.

EXAMPLE 22

Except that 5-(S)-2-propionyl-3-phenyl-1,3-diazabicyclo[3,3,0]octane was used in place of 5-(S)-2-acetyl-3-phenyl-1,3-diazabicyclo[3,3,0]octane and methylmagnesium iodide was used as the Grignard reagent, the procedure of Example 19 was followed to obtain (S)-2-benzyloxy-2-methylbutyraldehyde (41% yield); $[\alpha]_D = -39°$ (C=1.002, benzene); optical yield, 78%.

EXAMPLE 23

Except that 5-(S)-2-isobutyryl-3-phenyl-1,3-diazabicyclo[3,3,0]octane was used in place of 5-(S)-2-acetyl-3-phenyl-1,3-diazabicyclo[3,3,0]octane, the procedure of Example 18 was repeated to obtain (R)-2-hydroxy-2-phenyl-3-methylbutyraldehyde (75% yield); $[\alpha]_D = -308°$ (C=1.340, benzene); optical yield, 94% or more.

EXAMPLE 24

In 10 ml of ether, was dissolved 528 mg of 5-(S)-2-(5'-methyl-5'-hexanoyl)-3-phenyl-1,3-diazabicyclo-[3,3,0]octane. To the resulting solution cooled to −70° C., was added dropwise 1.5 equivalents of methylmagnesium bromide dissolved in ether. The mixture was allowed to react at −70° C. for one hour, then admixed with 5 ml of saturated aqueous ammonium chloride solution, and brought to room temperature. The ether layer was separated, admixed with 17 ml of 2% hydrochloric acid, and allowed to react at 0° C. for 3 hours. The ether layer was separated, washed with saturated aqueous sodium chloride solution, and dried over anhydrous sodium sulfate. The dried ether layer was freed from the ether by distillation under reduced pressure to obtain 250 mg of 2-hydroxy-2,6-dimethyl-6-heptenal. NMR peaks; δ (ppm)=1.3 (3H, singlet), 1.7 (3H, singlet), 1.4–1.8 (4H, multiplet), 2.0 (2H, triplet), 3.3 (1H, singlet), 4.6 (2H, broad singlet), 9.4 (1H, singlet).

What is claimed is:

1. A process for preparing an optically active or racemic α-hydroxyaldehyde represented by the general formula (2),

(2)

wherein $R_1$ represents a $C_6$–$C_{14}$ aryl group, $C_1$–$C_{10}$ alkyl group, $C_3$–$C_{10}$ alkenyl group, $C_2$–$C_{10}$ alkynyl group, $C_7$–$C_{14}$ aralkyl group, or a group containing a $C_1$–$C_4$ alkoxy or silyloxy group in the organic portion of said groups and $R_2$ represents a $C_1$–$C_{10}$ alkyl group, $C_2$–$C_{10}$ alkenyl group, $C_2$–$C_{10}$ alkynyl group, $C_7$–$C_{14}$ aralkyl group, $C_6$–$C_{14}$ aryl group, or a group containing a $C_1$–$C_4$ alkoxy or silyloxy group in the organic portion of these groups, which comprises allowing an optically active or racemic compound represented by the general formula (1),

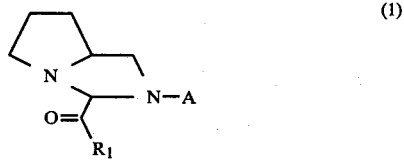

(1)

(wherein A represents a $C_6$–$C_{14}$ aryl group or a $C_1$–$C_4$ alkyl or alkoxy group- or halogen-substituted $C_6$–$C_{14}$ aryl group and $R_1$ is as defined above) to react with a Grignard reagent represented by the formula, $R_2MgX$ (wherein $R_2$ is as defined above and X is a halogen atom), and thereafter hydrolyzing the reaction product.

2. A process according to claim 1, wherein $R_1$ of the general formula (2) is the aryl group.

3. A process according to claim 1, wherein a compound represented by the general formula (1) in which A is as defined above and $R_1$ is a $C_6$–$C_{14}$ aryl group, is prepared by the reaction of an $C_6$–$C_{14}$ arylglyoxal with an optically active or racemic 2-(N-substituted aminomethyl)pyrrolidine represented by the general formula (3),

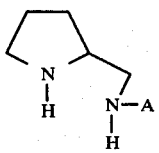
(3)

wherein A is as defined above.

4. A process according to claim 1, wherein a compound represented by the general formula (1) is prepared by allowing a Grignard reagent represented by the formula, $R_1MgX$ (wherein $R_1$ is as defined above and X is a haloge atom) to react with an optically active or racemic diazabicyclooctane derivative represented by the general formula (4),

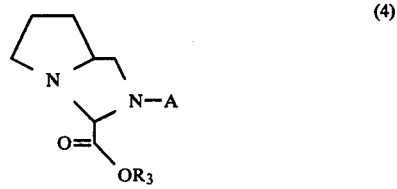
(4)

wherein $R_3$ represents a $C_1$–$C_4$ alkyl group and A is as defined above.

5. A process according to claim 4, wherein a compound represented by the general formula (4) is prepared by the reaction of a glyoxylate ester or a glyoxylate ester hemiacetal with an optically active or racemic 2-(N-substituted aminomethyl)pyrrolidine represented by the general formula (3), (3)

wherein A is as defined above.

6. A process according to claim 4, wherein the reaction of diazabicyclooctane derivative with Grignard reagent is carried out in the presence of a magnesium halide.

* * * * *